United States Patent [19]

Bicz

[11] Patent Number: 4,977,601
[45] Date of Patent: Dec. 11, 1990

[54] METHOD OF RECOGNIZING A FINGERPRINT

[75] Inventor: Wieslaw Bicz, Mainz, Fed. Rep. of Germany

[73] Assignees: Werner Pritzl; Bernd Wegener, both of Fed. Rep. of Germany; a part interest

[21] Appl. No.: 135,028

[22] PCT Filed: Mar. 26, 1987

[86] PCT No.: PCT/DE87/00134
§ 371 Date: Nov. 27, 1987
§ 102(e) Date: Nov. 27, 1987

[87] PCT Pub. No.: WO87/05790
PCT Pub. Date: Oct. 8, 1987

[30] Foreign Application Priority Data

Mar. 27, 1986 [DE] Fed. Rep. of Germany ....... 3610397

[51] Int. Cl.$^5$ .............................................. G06K 9/00
[52] U.S. Cl. .......................................... 382/4; 382/2; 356/71; 350/358
[58] Field of Search .................... 382/4, 2; 356/71; 350/358; 73/603, 620; 367/99

[56] References Cited

U.S. PATENT DOCUMENTS

| | | | |
|---|---|---|---|
| 3,614,737 | 10/1971 | Sadowsky | 382/2 |
| 4,053,228 | 10/1977 | Schiller | 356/71 |
| 4,385,831 | 5/1983 | Ruell | 382/4 |
| 4,631,965 | 12/1986 | De Vadder et al. | 73/603 |
| 4,785,667 | 11/1988 | Miyajima et al. | 73/620 |
| 4,876,725 | 10/1989 | Tomko | 382/4 |

OTHER PUBLICATIONS

Proceedings of the IEEE, Band 67, No. 4, Apr. 1979 (IEEE, New York, U.S.A.), M. Ahmed et al., "Holography and its Application to Acoustic Imaging", Seiten 466-483, siehe Zusammenfassung.

*Primary Examiner*—David K. Moore
*Assistant Examiner*—Yon Jung
*Attorney, Agent, or Firm*—Leydig, Voit & Mayer

[57] ABSTRACT

A method of detecting fingerprints by sensing scanning with ultrasonic waves. For comparison, an acoustic hologram of the characteristics of the respective finger is disposed in an identification card. The hologram is compared in a recognition device with an ultrasonic interference pattern which is obtained by reflection of ultrasonic waves at an interface formed between the surface of the finger and a planar application or support surface.

20 Claims, 8 Drawing Sheets

METHOD OF RECOGNIZING A FINGERPRINT

TECHNICAL FIELD

The invention relates to a method of recognizing fingerprints and similar skin surface structures in which the structure of a finger placed on a smooth surface is scanned and compared with a structure stored on a record carrier. The invention further relates to a system for carrying out such a method.

STATE OF THE ART

Devices for recognizing fingerprints are already known or have already been proposed in various forms. Thus, for example systems exist in which the fingerprint characteristics once detected are stored in a central computer from which the characteristics can be called up when required for comparison with the actual fingerprint which is obtained by a detection or scanning device. Such systems may however meet with objections for data protection reasons. For this reason systems have also been developed in which the characteristics of a fingerprint are recorded in a sort of identification card which the proprietor of the card himself inserts into a recognition device directly for comparison with his corresponding finger.

The comparison is carried out in the known systems in various manners. Thus, purely electronic methods are known as well as methods based mainly on optical scanning with only the final comparison of the data being made electronically. In purely electronic detection methods the scanning of the fingerprint can for example be carried out by capacitive or other correspondingly small sensors disposed in a matrix form. For optical detection prisms can be used against which the surface of the finger is pressed. In this case for example the prism surface changes its reflection behaviour at the areas at which the adjacent medium is no longer air but the raised areas of the finger surface bearing on the prism surface.

All these devices have the common disadvantage that they are relatively complicated in construction and thus cannot be built in simple forms which could be incorporated in mass production into small detection or scanning devices. A great number of these relatively complicated and thus also relatively exact detection devices can easily be connected to a data processing and data acquisition system. This advantage is however only necessary in specific cases and as already mentioned above the central acquisition of fingerprint data may meet with objections on the basis of the data protection laws.

EXPLANATION OF THE INVENTION

The invention is based on the problem of providing a method and a corresponding system for detecting fingerprints which permit simple construction so that a device made on the basis thereof can be made so that it is simple and reliable in its operation and economical to make and consequently can be used at any desired location independently of data processing systems. The important aspect is not to be the highest possible detection accuracy; on the contrary, a certain error frequency rate is admissible because a chance incorrect recognition need not necessarily involve direct disadvantageous consequences to the person allowing his finger to be compared with a data carrier. The error frequency rate can possibly be reduced in that several detection or scanning operations are admissible consecutively and it is thus sufficient for only the last such operation to be successful.

This problem is solved according to the invention by the method according to the characterizing clause of claim 1.

By using ultrasonic waves compared with light waves the following advantages are achieved in fingerprint recognition:

1. The fact that sound travels about five times slower in air than in water, to which substantially most parts of the human body also correspond, and that moreover no difficulties are involved in finding for the application or support plate for the finger a material which has similar sound propagation properties to water, makes it possible to achieve that at the transition point of the skin and application surface the soundwaves can readily pass with substantially the same velocity through the areas at which the raised areas of the skin of the finger directly contact the application surface but are reflected where the troughs of the finger structure are disposed, i.e. there is an air layer between the application surface and the skin.

2. Since the soundwaves travel slower and are longer than light waves, the analysis of the interference pattern can be carried out electronically in simple manner.

3. In contrast to light, with which holographic recordings are possible only by using laser light, when using acoustic holography no problems are encountered as regards the coherence of the waves.

4. Ultrasonic generators for frequencies in the range of 10–15 megahertz, which are preferred with the present method, are simple and cheap and can be very accurately controlled, making it possible for example to eliminate without any difficulties whatever reflexes and scattered waves. This also applies to sonic receivers. It is moreover possible to use the same element as sonic generator and sonic receiver.

5. When using acoustic holograms the calculations and production of the holograms are substantially easier than with optical holograms because the wavelength is greater.

6. The wavelength can be adapted to the structure of the surface of the finger and as a result the finger can be utilized as active element in the detection.

The scanning of fingerprints by means of soundwaves, in particular by means of such waves in the ultrasonic range, can be carried out according to the invention in three different manners.

The clearest form is the sensing of the finger surface dot-wise or line-wise by means of a focused ultrasonic beam by scanning. The necessary relative movement between the ultrasonic beam and the finger surface can be achieved by a mechanical movement of the finger support and/or a movement of the ultrasonic source. It is also possible to move the ultrasonic beam by pivoting a deflecting means in the wave path. A beam movement without mechanically moved parts an be achieved by controlled phase displacements in the wave front to be beamed. The intensity or contrast raster scanned by the ultrasonic beam is then subjected to a computer-aided evaluation for comparison with the stored data.

A further possibility of comparable acquisition of fingerprints by means of ultrasonic waves resides in subjecting the reflected soundwave structure physically or also computationally to a characteristic transformation, for example a Fourier transformation, to obtain a structure which is simpler for evaluation and comparison purposes. This is possible with finger surfaces because the latter due to their linear arrangement exhibit a predominantly periodic structure with which transformations of the type of a Fourier transformation are possible. Known fingerprint recognition methods aim solely at a direct comparison of the line arrays, in particular the detection of branch points. Hitherto, for recognizing fingerprints no use has been made of conversion of the structure of a finger surface to a simplified transformation image consisting substantially only of a dot raster.

The signals of the transformed structure can be transferred by a matrix receiver or a scanner to a computer which carries out the comparison with the stored data originating from a corresponding transformation.

Finally, acoustic holography can also be used for fingerprint detection.

The stored acoustic holograms of the finger surface used for the detection method can have a surface relief structure which corresponds to the characteristics of the finger and at which the soundwaves are differently reflected. For security reasons, such holograms in which the characteristic structure is visually embossed in the surface are not very appropriate. Consequently, acoustic holograms are to be preferred which seen from the outside have a planar surface beneath which however materials of different sound propagation properties are to be used. In holograms which are traversed by the ultrasonic waves areas of different acoustic transparency may be employed.

The path of the soundwaves and the arrangement of the individual elements in the detection system may be chosen in various manners. It is for example possible to transmit the soundwave fronts coming from the ultrasonic generator or the ultrasonic source firstly through the record carrier containing the acoustic hologram and then allow them to pass through the finger application or support plate to the finger boundary face from which the soundwaves are then reflected variably corresponding to the finger surface structure and supplied to an ultrasonic raster receiver. The converse arrangement is however also possible in which the soundwaves are first transmitted onto the finger boundary face and the waves reflected there then sent through the hologram in order to impinge on the raster receiver on the outlet side.

A further method resides in using the record carrier containing the acoustic hologram directly as finger application plate. In this arrangement the soundwaves are directed from the side of the acoustic hologram remote from the finger application surface against said hologram and the waves reflected by the hologram and the finger boundary face are received in a receiver.

Finally, an arrangement is also possible in which the soundwaves coming from the sound source are directed simultaneously on the one hand onto the finger boundary face and on the other onto a reflecting hologram. The soundwaves reflected from the two surfaces are then supplied to the raster receiver. A variant of this arrangement resides in that the sonic generator and sonic receiver lie substantially in the same plane and the soundwaves are directed in the configuration of an equilateral triangle from there onto the finger boundary face, from the latter onto the hologram and back to the receiver and at the same time in the reverse direction.

In the case where the sonic generator and receiver are one and the same component by the pulse technique the operation is carried out intermittently whereas with separate receivers the sonic generator can also operate with continuous sonic radiation.

It is of particular advantage to the mode of operation of the system for the entire measuring arrangement in so far as the course of the ultrasonic waves is concerned, that is essentially the ultrasonic generator and receiver, to be located in liquid, preferably water. The liquid in such cases extends up to the rear side of the finger application plate which, as already mentioned above, is to consist of a material whose sound propagation speed substantially corresponds to that of the liquid to avoid an additional interface transition. Instead of a liquid, for example, it is also possible to use a solid preferably plastic material with corresponding properties into which the measuring arrangement is embedded or to which the sonic generator or receiver is coupled.

BRIEF DESCRIPTION OF THE DRAWINGS

Hereinafter the method according to the invention will be explained in detail with the aid of the attached drawings, wherein.

PRACTICAL EMBODIMENTS OF THE INVENTION

Figure 1:
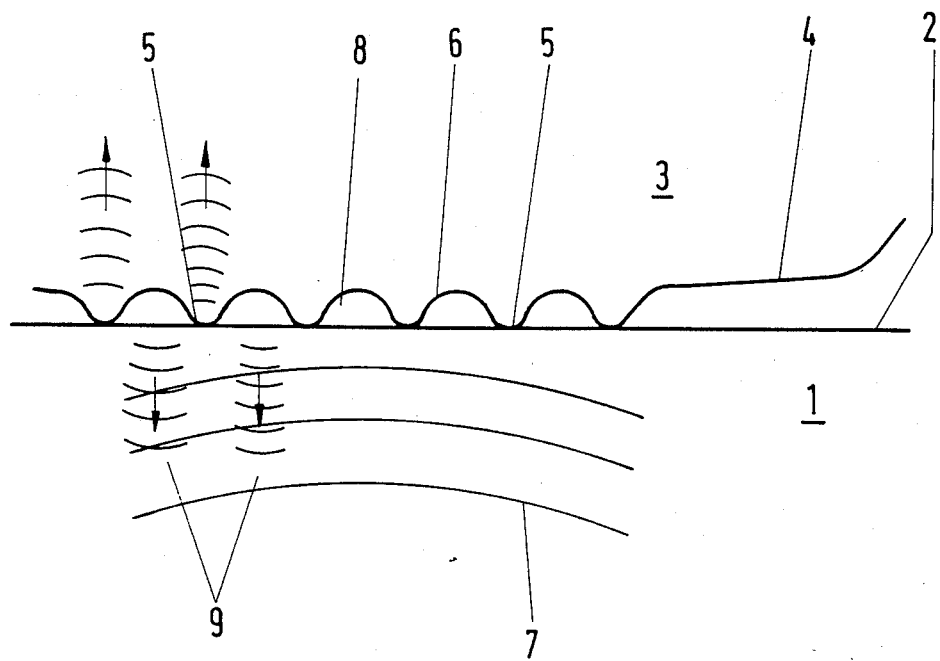
FIG. 1 is a schematic illustration of the conditions indicating how ultrasonic waves are reflected at the interface between a finger surface and a planar support surface.

FIG. 1 shows without its lower border a support or application plate 1 which has a planar surface 2. Bearing on the surface 2 is a portion 3 of a human finger. The surface 4 of the finger comprises raised or peak areas 5 and lower or trough areas 6. Through the application plate 1, the material of which has as far as possible a sound propagation speed corresponding substantially to that of water, a front of ultrasonic waves 7 in the frequency range of 10 to 15 megahertz is transmitted which impinges on the interface between the application plate 1 and finger surface 4. At the points at which the raised areas 5 of the finger surface are in direct contact with the surface 2 of the application plate 1 the ultrasonic waves pass to a great extent through the interface between finger and application plate and propagate themselves within the finger with substantially the same velocity if the sound propagation velocity in the application plate 1 substantially corresponds to that within the finger. However, in the regions of the depressions 6 of the finger surface, in which behind the surface 2 of the application plate 1 air spaces 8 are disposed, the soundwaves are reflected in the form of local wave fronts due to the substantially smaller propagation velocity in air. These wave fronts 9 form a specific interference structure which is picked up by a raster receiver disposed in the propagation path of the wave fronts 9.

In the following Figures various arrangements for the soundwave path in the system according to the invention are shown.

Figure 2:
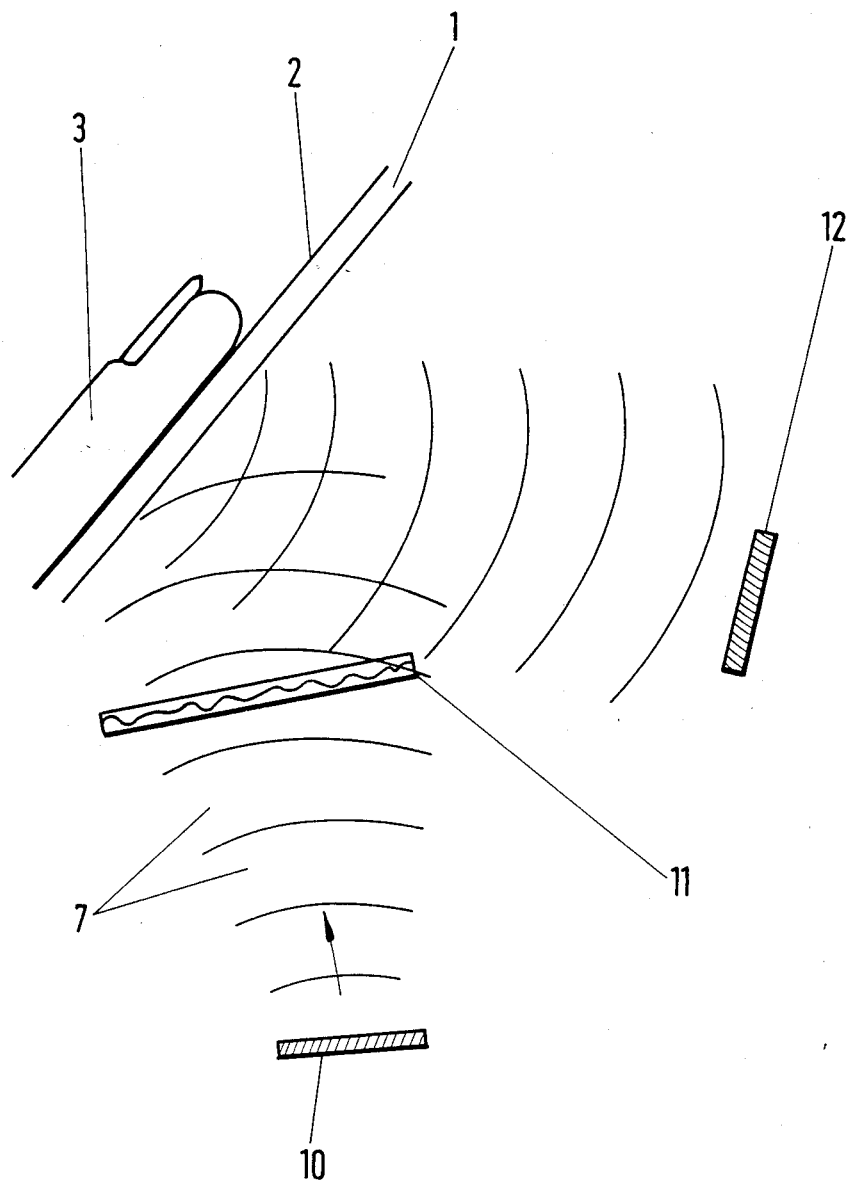
FIG. 2 shows a first arrangement for the soundwave path in the detection of fingerprints by means of acoustic holography.

In the arrangement according to FIG. 2 the soundwaves 7 generated by a first ultrasonic generator 10 first impinge on a card 11 containing the acoustic hologram of the fingerprint. The soundwaves passing through the card 11 then reach the interface between the application plate 1 and the finger 3. In the direction of the soundwaves reflected by said interface there is a raster receiver 12 with which the interference pattern obtained can be picked up.

Figure 3:
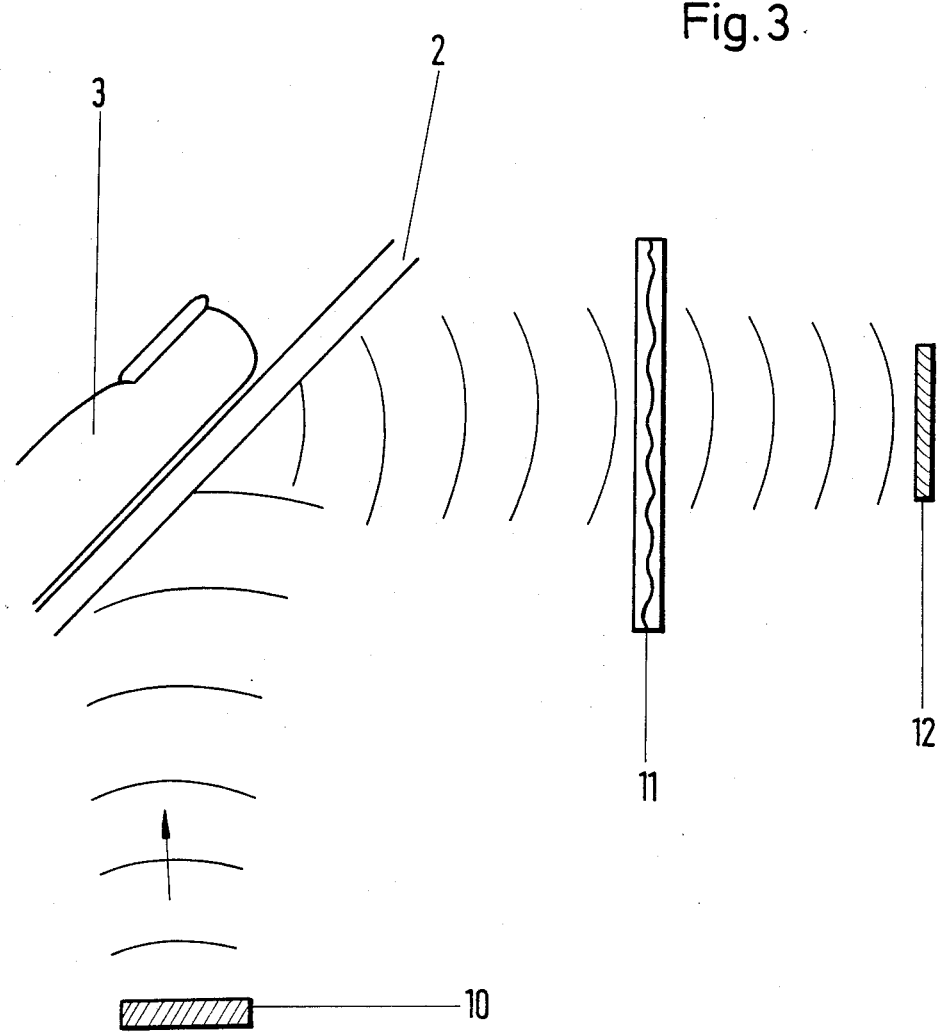
FIG. 3 shows a second possible arrangement for the path of soundwaves with the holographic method.

The arrangement according to FIG. 3 differs from that according to FIG. 2 only in that the soundwaves firstly impinge on the interface between the finger and application plate and only then do the reflected soundwaves pass through the card 11 containing the acoustic hologram.

Figure 4:
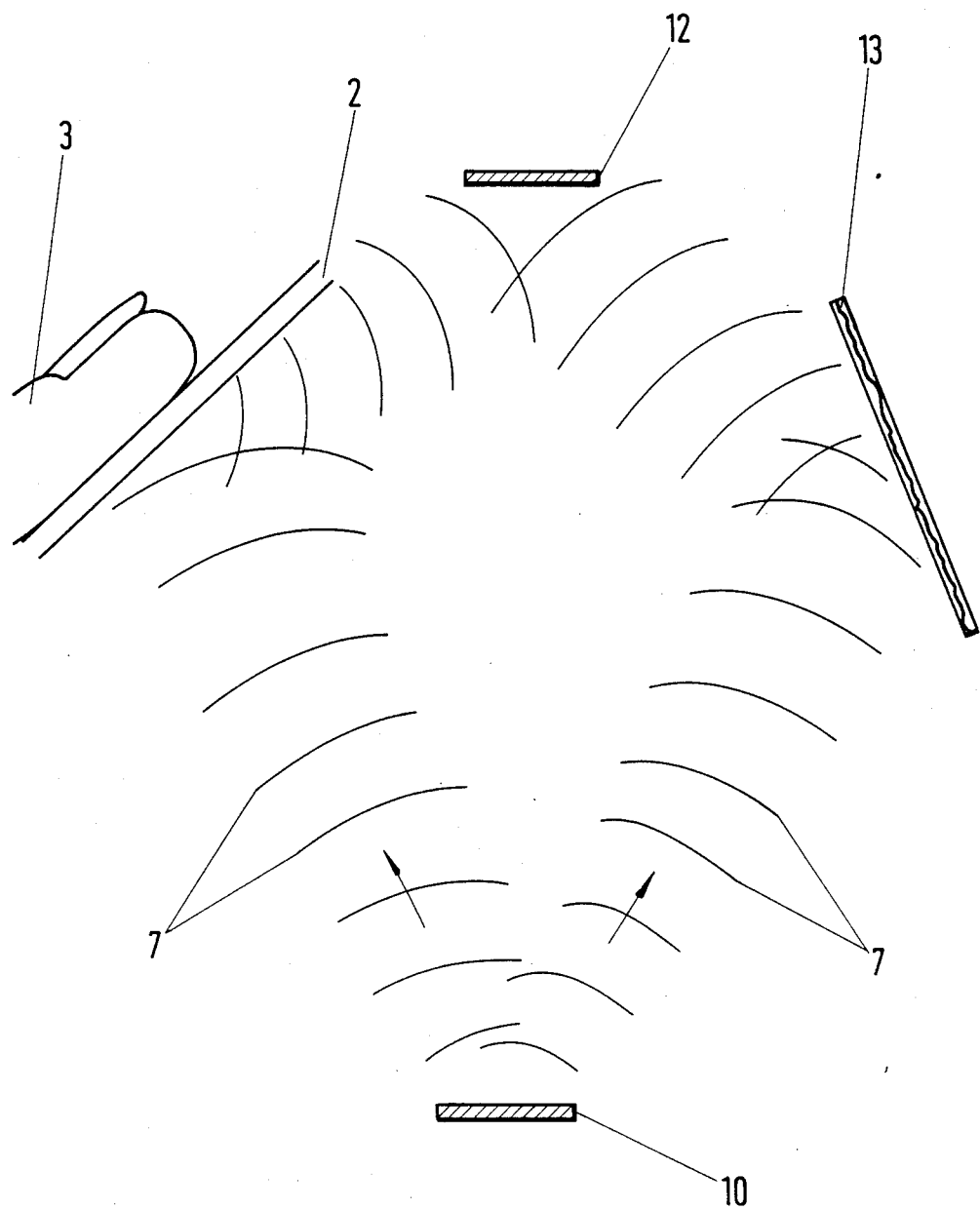
FIG. 4 is a third possible arrangement for the path of the soundwaves in the holographich method.

In FIG. 4 an arrangement is shown in which the soundwaves 7 of the wave front generated by the ultrasonic generator 10 are sent directly both to the interface between the finger 3 and the support surface 2 and to a card 13 which contains an acoustic hologram but at which in contrast to the two previously described embodiments the soundwaves are also reflected. The two reflected waves interfere with each other and are acquired by the receiver 12. The total sonic wave path is expediently in a liquid whose sound propagation velocity corresponds substantially to that of the finger application plate.

Figure 5:
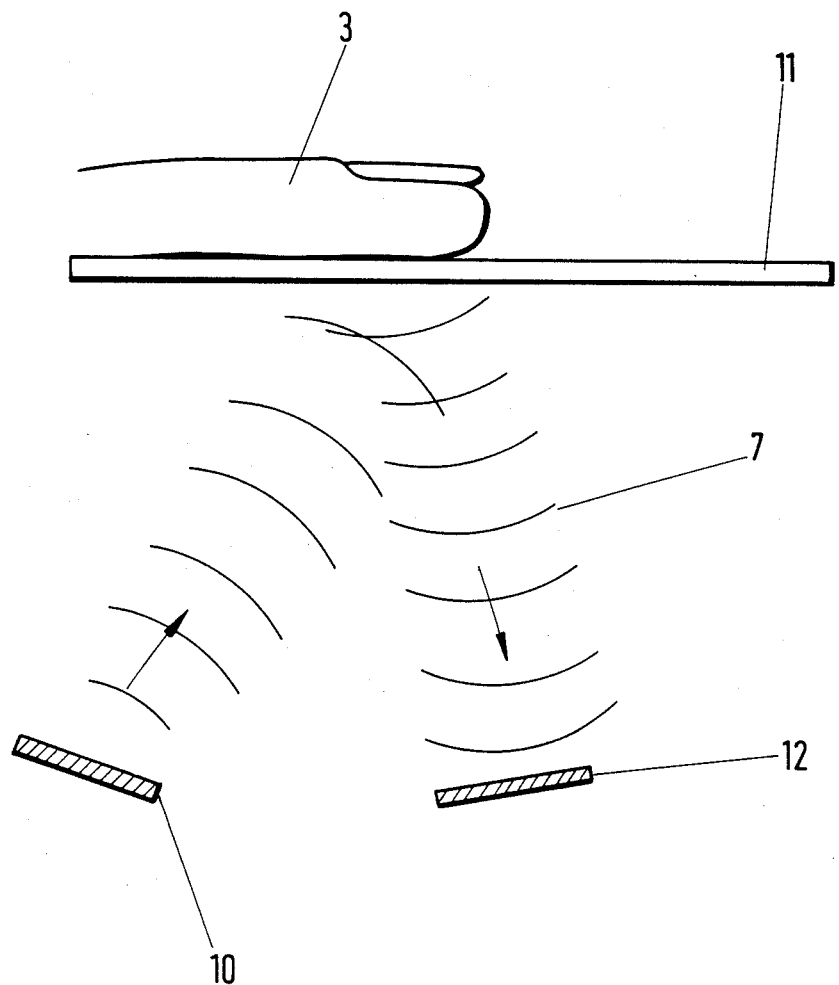
FIG. 5 is a fourth possible arrangement for the path of the soundwaves in the holographic method.

In the arrangement according to FIG. 5 the card 11 containing the acoustic hologram is used directly as application surface for the finger 3. The soundwaves 7 pass through the card, are partially reflected at the interface between finger and card and the reflected waves picked up by the receiver 12.

Figure 6:
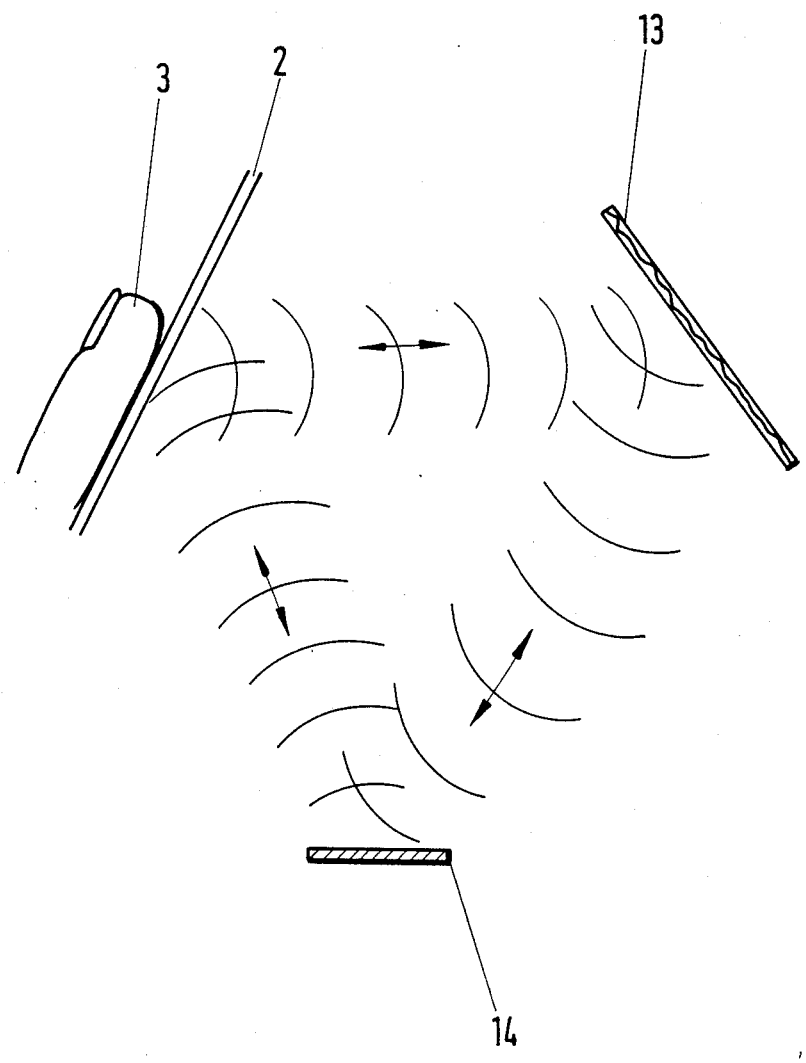
FIG. 6 is a fifth possibility for the arrangement of the path of the soundwaves in the holographic method.

Finally, a last embodiment is shown in FIG. 6. In this case the sonic generator and receiver are combined together to form a unit 14. This unit transmits soundwaves both against the interface between the application surface 2 and finger 3 and against the card 13 containing an acoustic reflection hologram. Due to the symmetrical arrangement in the form of an equilateral triangle on the one hand soundwaves are reflected from the finger boundary face to the card 13 and on the other also reflected from said card to the finger boundary face, the particular soundwaves reflected there being reflected back again to the transmitter/receiver.

The raster or scanning receivers for the ultrasonic waves may for example consist of a raster or grid of small piezoelectric receiver elements in which the particular sonic pressure impinging on a raster unit is converted to an electrical signal. The grid or raster obtained of electrical signals is then supplied to an electronic evaluating unit which is not illustrated and which carries out the necessary comparison electronically.

Figure 7:
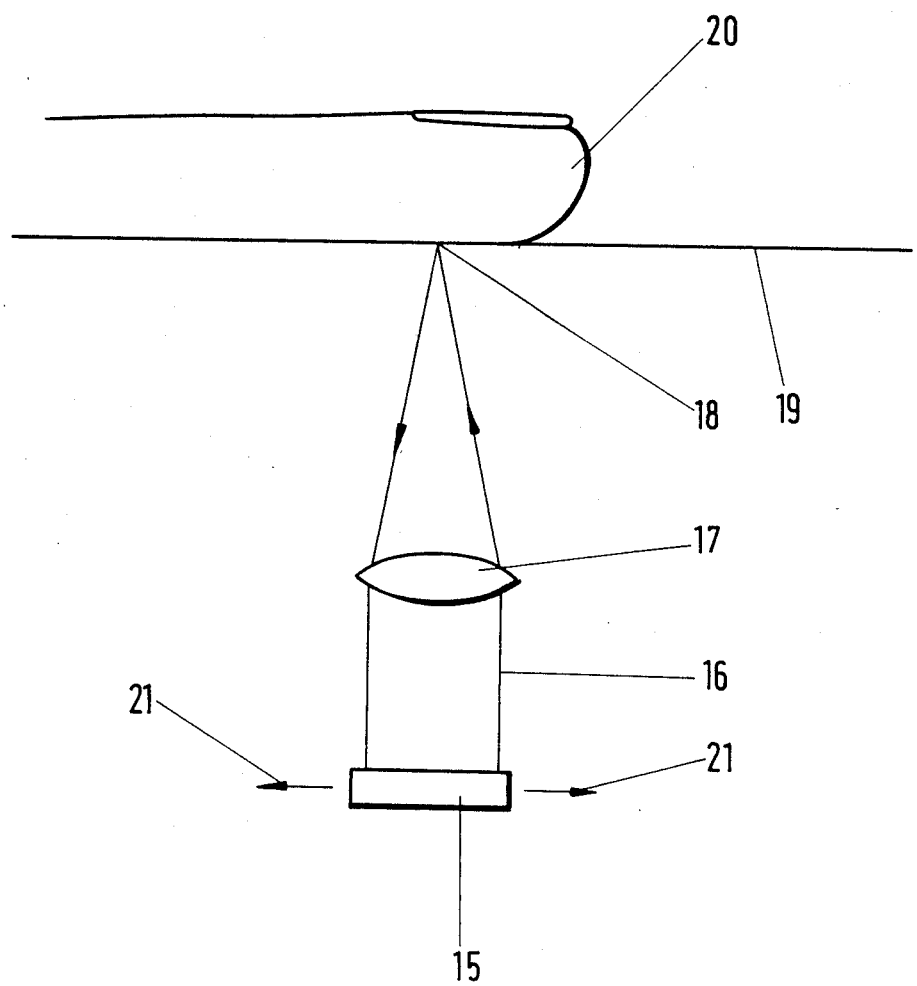
FIG. 7 is a schematic arrangement of the scanning of a finger surface by means of a focused ultrasonic beam and FIG. 8 is a schematic arrangement for a physical transformation of an ultrasonic structure reflected by a finger surface.

FIG. 7 is a schematic arrangement for scanning a finger surface by means of collimated ultrasonic radiation. A combined ultrasonic transmitter and receiver 15 transmits an ultrasonic wave front 16 which is focused through a lens arrangement 17 focusing soundwaves onto a point 18 which is adjusted to the interface between a contact face 19 and the surface of a finger 20.

The sound reflected by the point 18 is conducted to the transmitter/receiver 15 again as indicated by the oppositely directed arrows in the beam path. The transmitter/receiver 15 is designed for intermittent transmitting and receiving so that the scanning is carried out pulsewise. The arrows 21 are intended to indicate that the sound source 15 is reciprocated for scanning the finger surface.

Figure 8:
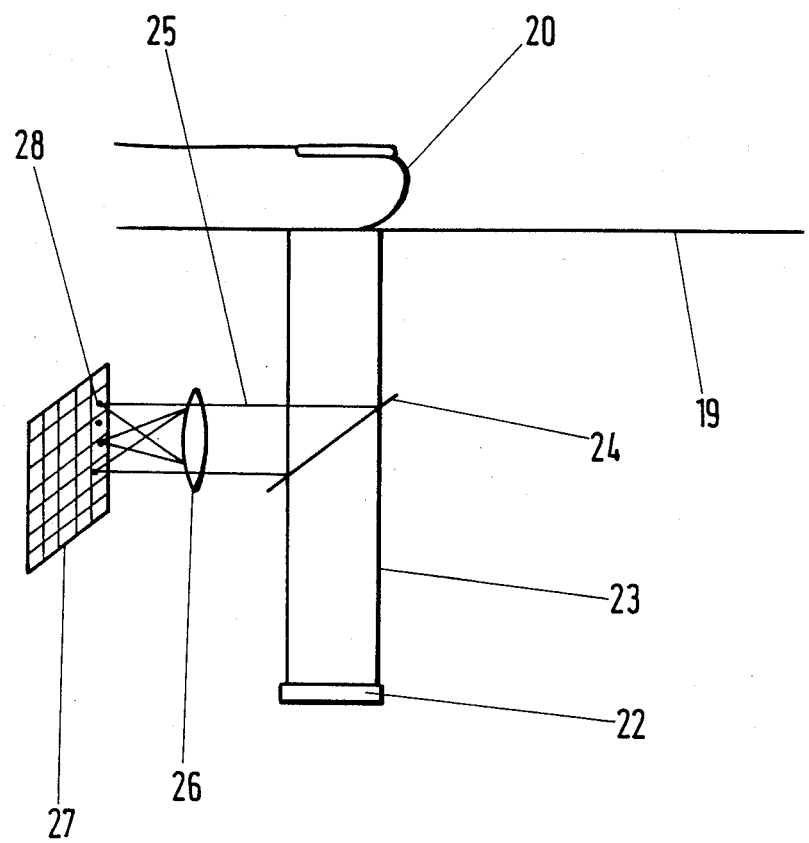

FIG. 8 illustrates an acquisition means with physical transformation of the reflected wave structure. An ultrasonic transmitter 22 transmits a wave front 23 which is directed through a mirror 24 permeable in this direction onto the interface between the contact face 19 and the surface of the finger 20. The wave front reflected by the interface is at least partially deflected at the mirror 24 and as wave front 25 supplied to a physical transformation element 26 in the form of an acoustic lens arrangement. On a collecting face 27, for example an acoustic-electrical transducer matrix, a structure image simplified by the transformation arises in the form of a dot raster 28 which can be evaluated in simple manner, i.e. by comparison with a stored characteristic raster generated in corresponding manner.

I claim:

1. Method of recognizing fingerprints and similar skin surface structures in which the structure of a finger surface placed on a smooth surface is scanned and compared with a characteristic structure stored on a record carrier, characterized in that the structure of the finger surface is scanned with soundwaves generated by an ultrasound source, the soundwaves being directed through a liquid and/or solid body at least from the ultrasound source to the smooth surface and being directed through the smooth surface to the finger surface, the soundwave structure obtained being transformed to suitable evaluation characteristics and being compared with the stored characteristic structure.

2. Method according to claim 1, characterized in that ultrasonic waves in a frequency range of 10-15 megahertz are used.

3. Method according to claim 1, characterized in that the finger surface is sensed with a focused sonic beam by so-called scanning effecting relative movement between the focused sonic beam and the finger surface.

4. Method according to claim 3, in which said focused sonic beam extends along a path and has an end point, said method being characterized in that the relative movement between the focused sonic beam and the finger surface is generated by a movement of the finger, the ultrasound source and/or a deflection element disposed in the path of the sonic beam.

5. Method according to claim 3, characterized in that a movement of the end point of the focused sonic beam is effected by phase displacements within the soundwave front generated.

6. Method according to claim 3, characterized in that acoustic signals in said sonic beam are converted to electrical signals and evaluated in a computer for structure analysis.

7. Method according to claim 1, characterized in that the soundwave structure reflected by the finger surface is subjected by suitable physical transducer or converter elements to a characteristic transformation, for example to a Fourier transformation, and the transformed structure is converted by means of a scanning or matrix receiver to a signal image.

8. Method according to claim 1, in which there is an interface between said finger surface and said smooth surface, said method being characterized in that said record carrier contains the characteristics of the finger surface in the form of an acoustic hologram, there being ultrasonic interference reflected by the interface between the finger surface and the smooth surface, said ultrasonic interference being compared with the acoustic hologram in the record carrier.

9. Method according to claim 8, characterized in that for the characteristic comparison the soundwaves generated by said ultrasonic source are directed against the acoustic hologram, the soundwaves passing through the hologram being directed onto said finger surface, and the soundwaves reflected by said finger surface being picked up by a raster receiver.

10. Method according to claim 8, characterized in that for the characteristic comparison the soundwaves generated by said ultrasonic source are first directed onto said finger surface and the soundwaves reflected from there are passed through the acoustic hologram, the soundwaves emerging from the hologram being picked up by a raster receiver.

11. Method according to claim 8, characterized in that the soundwaves generated by said ultrasonic source are directed both onto said finger surface and onto the acoustic hologram and the soundwaves reflected from both are picked up by a raster receiver.

12. Method according to claim 8, characterized in that the soundwaves are generated by said ultrasonic source in symmetrical arrangement of an equilateral triangle and are first directed onto said finger surface, the soundwaves reflected by said finger surface being directed onto the hologram, and the soundwaves reflected by the hologram being directed back to a matrix receiver.

13. Method according to claim 12, characterized in that the sonic source is simultaneously used as receiver.

14. A system of recognizing fingerprints and similar skin surface structures, said system comprising an application plate (1) made of a material transparent to ultrasonic waves and having a smooth surface (2) for supporting a finger (3), a record carrier (11, 13) having a acoustic hologram containing the characteristics of a fingerprint, an ultrasonic generator (10) for producing ultrasonic energy, a raster receiver (12) for converting ultrasonic energy to electrical signals, the soundwaves emitted by said ultrasonic generator being directed through a liquid and/or solid body at least from said ultrasonic generator to said smooth surface with at least some of the soundwaves passing through said smooth surface, the soundwaves emitted by said generator impinging successively or simultaneously on the finger surface and the acoustic hologram, the soundwaves reflected thereby being supplied to said raster receiver, and an electronic evaluating unit for evaluating said signals from said raster receiver.

15. System according to claim 14, characterized in that the material of the application plate (1) has a sound velocity which is greater, preferably five times greater, than that of air.

16. System according to claim 14, characterized in that the acoustic hologram is adapted to be traversed by means of ultrasonic waves.

17. System according to claim 14, characterized in that the acoustic hologram contains the fingerprint characteristics as regions of higher and lower sonic transparency or sound velocity.

18. System according to claim 14, characterized in that the ultrasonic generator (10) is constructed simultaneously as sonic receiver (14).

19. System according to claim 14, characterized in that the ultrasonic generator is coupled to a liquid or a plastic which extends up to the application plate.

20. System according to claim 14, characterized in that in addition sound-focusing and sound-reflecting elements are provided.

* * * * *